United States Patent [19]

Hatono et al.

[11] Patent Number: 4,810,422

[45] Date of Patent: Mar. 7, 1989

[54] BILE ACID DERIVATIVES, THEIR SALTS AND PRODUCTION THEREOF

[75] Inventors: Shunsou Hatono; Akira Yazaki; Masaharu Yokomoto; Yuzo Hirao, all of Koda, Japan

[73] Assignee: Wakunaga Seiyaku Kabushiki Kaisha, Osaka, Japan

[21] Appl. No.: 91,957

[22] Filed: Sep. 1, 1987

[30] Foreign Application Priority Data

Sep. 5, 1986 [JP] Japan .................... 61-208901

[51] Int. Cl.$^4$ .............................................. C07J 1/00
[52] U.S. Cl. ................................................ 260/397.1
[58] Field of Search ..................................... 260/397.1

[56] References Cited

FOREIGN PATENT DOCUMENTS 66924 10/1978 Romania ................ 260/397.1
8600311 1/1986 U.S.S.R.

OTHER PUBLICATIONS

Carroll et al., Journal of Medicinal Chemistry, 1972, 15 (11), pp. 1158–1161.
Niculescu-Duvaz et al., J. Prakt. Chem., 1979, 321 (3), pp. 522–528.
Wolf et al., J. Org. Chem., 1973, 38 (7), pp. 1276–1279.
Baracu et al., Rev. Roum. Chim., 1985, 30 (4), pp. 317–327.
Chemical Abstracts; vol. 103, (1985), #134470g; Baracu et al.
Chemical Abstracts; vol. 98, (1983), #179757a; Niculescu-Duvaz et al.
Chemical Abstracts; vol. 91, (1979), #211670k; Niculescu-Duvaz et al.
Chemical Abstracts; vol. 79, (1973), #136513n; Wolf et al.

Primary Examiner—Leonard Schenkman
Assistant Examiner—Joseph A. Lipovsky
Attorney, Agent, or Firm—Wenderoth, Lind & Ponack

[57] ABSTRACT

A bile acid derivative of the following formula (I):

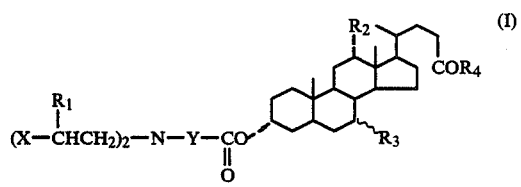

wherein: X is a halogen atom; $R_1$ is a hydrogen atom or a lower alkyl group; Y is

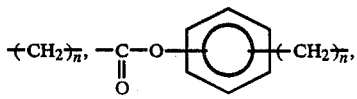

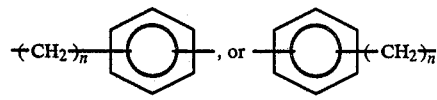

(wherein n is an integer of from 0 to 5); each of $R_2$ and $R_3$ is a hydrogen atom or a hydroxyl group; $R_4$ is a hydroxyl group, lower alkoxyl group,

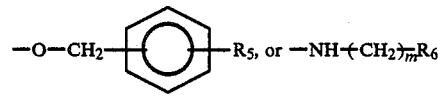

(wherein $R_5$ is a hydrogen atom or a lower alkoxy group, $R_6$ is a carboxyl group, benzyloxycarbonyl group or sulfonyl group, or a salt thereof, and m is an integer of from 1 to 4); the intermittent line, . . . , is an α-bond; and the wavy line, ∼∼∼, is an α- or β-bond, and a salt thereof, and a process for production thereof.

This bile acid derivative has carcinostatic activity and yet is of low toxicity. Accordingly, this compound can be used as a carcinostatic agent.

4 Claims, No Drawings

BILE ACID DERIVATIVES, THEIR SALTS AND PRODUCTION THEREOF

BACKGROUND OF THE INVENTION

This invention relates to novel bile acid derivatives and production thereof. These bile acid derivatives are useful as therapeutical drugs for cancers.

Bile acids are one kind of steroid compounds, constituting the main components of bile of vertebrate animals. Most of these bile acids have been known to be generally hydroxylated derivatives of 5β-cholanic acid having 24 carbon atoms.

In human bile, cholic acid, deoxycholic acid, chenodeoxycholic acid, lithocholic acid and the like are contained, but slight differences can be seen in the kind and composition of bile acids depending on the species of animals (for example, there exist species specific bile acids such as ursodeoxycholic acid in the bile of bears and β-muricholic acid in the bile of rats).

These bile acids are essential components absolutely required for absorption of fats or vitamins and control of lipid metabolism in living bodies, and among them, dehydrocholic acid and ursodeoxycholic acid have been frequently used for the purpose of promoting bile secretion, dissolution of gallstone, lipid digestion and absorption, conditioning of intestine, etc.

On the other hand, as for the distribution of bile acids, they are synthesized from cholesterol in the liver and, after being conjugated with glycine or taurine, secreted into the bile and stored and concentrated within the gallbladder, and thereafter released into the duodenum. Bile acids have been known to be absorbed through the ileum after having fulfilled functions such as emulsification (solubilization) of substances insoluble in water in the small intestine, enter the portal vein, be taken up in the liver cells and again secreted into the bile (circulation of intestine-portal vein-liver-bile duct, namely, enterohepatic circulation).

Recently, studies have been made on the derivatives utilizing the unique functions possessed by the bile acids as described above. For example, Ito et al. synthesized compounds in which iminodiacetic acid is bound to the 23-position carboxyl group of naturally occurring bile acids, and reported that they are useful as gallstone dissolving agents on the basis of the finding that they have a remarkable calcium carbonate dissolving activity (see Japanese Patent Laid-Open Publications Nos. 161996/1985 and 163896/1985). However, concerning the derivatives in which N-haloalkylamino acid is bound by the ester bond to the 3-position hydroxyl group of naturally occurring bile acids, they have not even existed themselves as far as we are aware, nor has there been any report up to date about the fact that carcinostatic activity is found in the natural bile acids or their derivatives.

SUMMARY OF THE INVENTION

This invention is concerned with the bile acid derivatives having an amino acid having a nitrogen mustard moiety ester-bound to the 3-position hydroxyl group of bile acids and their salts.

More particularly, the bile acid derivatives according to the present invention are represented by the following formula (I):

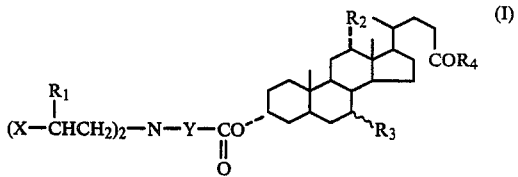

wherein: X is a halogen atom; $R_1$ is a hydrogen atom or a lower alkyl group; Y is

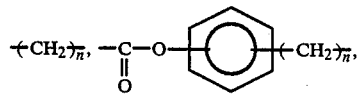

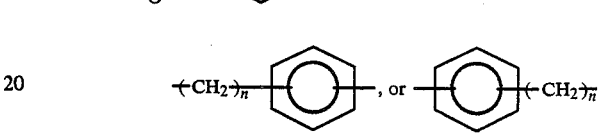

(wherein n is an integer of 0 to 5); each of $R_2$ and $R_3$ is a hydrogen atom or a hydroxyl group; $R_4$ is a hydroxyl group, lower alkoxyl group,

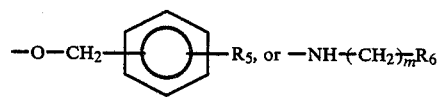

(wherein $R_5$ is a hydrogen atom or a lower alkoxyl group, $R_6$ is a carboxyl group, benzyloxycarbonyl group or sulfonyl group, or its salt, m is an integer of 1 to 4); the intermittent line, . . . , is an α-bond; and the wavy line, ∿∿, is an α- or β-bond.

Further, the process for producing the bile acid derivatives of the above formula (I) or their salts according to the present invention comprises the step (a), the steps of (a) and (b), or the steps (a), (b) and (c) set forth below:

(a) causing a bile acid derivative of the following formula (II):

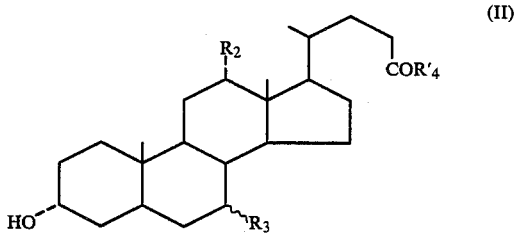

wherein: each of $R_2$ and $R_3$ is a hydrogen atom or a hydroxyl group; $R'_4$ is a lower alkoxyl group or

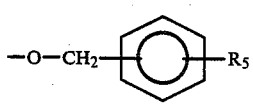

(wherein $R_5$ is a hydrogen atom or a lower alkoxyl group); the intermittent line, . . . , is an α-bond, and the wavy line, ∿∿, is an α- or β-bond, to react with a compound of the following formula (III):

 (III)

wherein: X is a halogen atom; $R_1$ is a hydrogen atom or lower alkyl group; and Y is

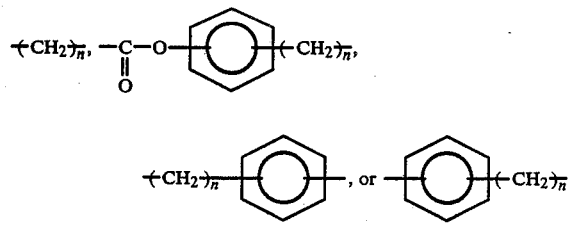

(wherein n is an integer of 0 to 5), thereby to obtain the bile acid derivative of the above formula (I) (wherein $R_4$ is the same as $R'_4$);

(b) subjecting the bile acid derivative obtained in the above step (a) wherein $R_4$ is

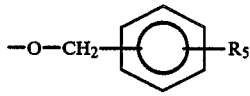

to acid treatment or to catalytic reduction to obtain the bile acid derivative of the above formula (I) (wherein $R_4$ is a hydroxyl group); and (c) causing the bile acid derivative obtained in the preceding step (b) to react with a compound of the formula (IV):

 (IV)

wherein $R_6$ is a carboxyl group, benzyloxycarbonyl group or sulfonyl group which may be in salt form, and m is an integer of 1 to 4, to obtain the bile acid derivative of the above formula (I) (wherein $R_4$ is —NH—$(CH_2)_m$—$R_6$.

The bile acid derivatives and their salts according to the present invention are expected to contribute greatly to cancer disease countermeasures, particularly therapy and prophylaxis of liver-bile duct system cancer diseases, partly because enterohepatic circulation may be predicted since they are derived from naturally occurring bile acids (e.g., cholic acid, deoxycholic acid, ursodeoxycholic acid, chenodeoxycholic acid and lithocholic acid) and partly because they have per se carcinostatic activity.

DETAILED DESCRIPTION OF THE INVENTION

Bile acid derivatives

The bile acid derivatives according to the present invention are represented by the above formula (I). (The definitions of the symbols in the formula are also as defined above.)

The present invention also encompasses salts of these compounds. More particularly, the compounds of the formula (I), in the case where $R_4$ has an acid base such as a carboxyl group, can be salts with alkali metals or alkaline earth metals such as sodium, potassium and magnesium, or salts with any of pharmaceutically acceptable bases such as ammonium salts and amine salts, and, by virtue of a tertiary amine group in the nitrogen mustard moiety, can also be salts with any of pharmaceutically acceptable acids such as hydrochloric acid, sulfuric acid and like inorganic acids, formic acid and malonic acid.

Specific examples of these compounds are tabulated below together with the data on the $^1$H-NMR spectra thereof and the Rf values thereof obtained by thin layer chromatography.

TABLE 1

| Example No. | X | R$_1$ | Y | R$_2$ | R$_3$ | R$_4$ | $^1$H-NMR Spectrum δ·TMS | | | | | | | TLC R$_f$ Value |
|---|---|---|---|---|---|---|---|---|---|---|---|---|---|---|
| | | | | | | | 3-H | 7-H | 12-H | 18-CH$_3$ | 19-CH$_3$ | 21-CH$_3$$^a$ | R$_4$ | (X—⟨⟩—CH—CH$_2$)$_2$—N—Y—COO—  (with R$_1$) | |
| 1 | Cl | H | —⟨⟩—CH$_2$— | OH | α-OH | O—CH$_2$—⟨⟩—OCH$_3$ | 4.58 | 3.85 | 3.97 | 0.67 | 0.90 | 0.97 | 7.30(d, J=8.5Hz, 2H) 6.89(d, J=8.5Hz, 2H) 5.05$^b$(2H) 3.81(s, 3H) | 7.15(d, J=8.5Hz, 2H) 6.62$^c$(d, J=8.5Hz, 2H) 3.66$^c$(8H, max, 3.71, 3.68, 3.64, 3.62) 3.46(s, 2H) | — |
| 2 | Cl | H | —⟨⟩—CH$_2$— | OH | α-OH | OH | 4.58 | 3.87 | 4.00 | 0.70 | 0.90 | 1.00 | — | 7.15(d, J=8.5Hz, 2H) 6.62$^c$(d, J=8.5Hz, 2H) 3.66$^c$(8H, max, 3.71, 3.68, 3.64, 3.61) 3.46(s, 2H) | 0.42 |
| 3 | Cl | H | —⟨⟩—CH$_2$— | H | α-OH | O—CH$_2$—⟨⟩ | 4.58 | 3.82 | X | 0.63 | 0.90 | 0.93 | 7.34(br, s, 5H) 5.10$^b$(2H) | 7.15(d, J=8.5Hz, 2H) 6.63(d, J=8.5Hz, 2H) 3.64$^c$(8H, max, 3.68, 3.64, 3.62, 3.60) 3.46(s, 2H) | — |
| 4 | Cl | H | —⟨⟩—CH$_2$— | H | α-OH | OH | 4.58 | 3.86 | X | 0.66 | 0.91 | 0.94 | — | 7.15(d, J=8.5Hz, 2H) 6.63$^c$(d, J=8.5Hz, 2H) 3.66$^c$(8H, max, 3.70, 3.68, 3.64, 3.62) 3.47(s, 2H) | 0.57 |
| 5 | Cl | H | —⟨⟩—CH$_2$— | H | β-OH | O—CH$_2$—⟨⟩—OCH$_3$ | 4.67 | X | X | 0.65 | 0.95 | 0.91 | 7.29(d, J=8.5Hz, 2H) 6.88(d, J=8.5Hz, 2H) 5.04$^b$(2H) 3.81(s, 3H) | 7.16(d, J=8.5Hz, 2H) 6.64(d, J=8.5Hz, 2H) 3.67$^c$(9H, max, 3.72, 3.69, 3.65, 3.62) 3.48(s, 2H) | — |
| 6 | Cl | H | —⟨⟩—CH$_2$— | H | β-OH | OH | 4.67 | X | X | 0.68 | 0.95 | 0.94 | — | 7.15(d, J=8.5Hz, 2H) 6.63$^c$(d, J=8.5Hz, 2H) 3.66$^c$(9H, max, 3.70, 3.68, 3.64, 3.61) 3.48(s, 2H) | 0.45 |
| 7 | Br | H | —⟨⟩—CH$_2$— | OH | α-OH | O—CH$_2$—⟨⟩—OCH$_3$ | 4.58 | 3.86 | 3.97 | 0.66 | 0.89 | 0.96 | 7.29(d, J=8.5Hz, 2H) 6.88(d, J=8.5Hz, 2H) 5.04$^b$(2H) 3.80(s, 3H) | 7.14(d, J=8.5Hz, 2H) 6.61(d, J=8.5Hz, 2H) 3.74(t, J=7.5Hz, 4H) 3.45(s, 2H) 3.43(t, J=7.5Hz, 4H) | — |

TABLE 1-continued

| Example No. | X | R₁ | Y | R₂ | R₃ | R₄ | 3-H | 7-H | 12-H | 18-CH₃ | 19-CH₃ | 21-CH₃[a] | R₄ | R₁ — (X—CH—CH₂)₂—N—Y—COO— | TLC R_f Value |
|---|---|---|---|---|---|---|---|---|---|---|---|---|---|---|---|
| 8 | Br | H |  | OH | α-OH | OH | 4.58 | 3.86 | 4.00 | 0.70 | 0.90 | 0.99 | — | 7.15(d, J=8.5Hz, 2H) 6.62(d, J=8.5Hz, 2H) 3.75(t, J=7.5Hz, 4H), 3.46(s, 2H) 3.44(t, J=7.5Hz, 4H) | 0.41 |
| 9 | Br | H |  | OH | H | OH | 4.71 | X | 3.96 | 0.64 | 0.90 | 0.95 | 7.28(d, J=8.5Hz, 2H) 6.87(d, J=8.5Hz, 2H) 5.04ᵇ(2H) 3.79(s, 3H) | 7.15(d, J=8.5Hz, 2H) 6.62(d, J=8.5Hz, 2H) 3.74(t, J=7.5Hz, 4H) 3.46(s, 2H) 3.43(t, J=7.5Hz, 4H) | — |
| 10 | Br | H |  | OH | H | OH | 4.71 | X | 4.00 | 0.68 | 0.91 | 0.98 | — | 7.15(d, J=8.5Hz, 2H) 6.62(d, J=8.5Hz, 2H) 3.75(t, J=7.5Hz, 4H) 3.47(s, 2H) 3.44(t, J=7.5Hz, 4H) | 0.59 |
| 11 | Cl | CH₃ |  | OH | H | OH | 4.72 | X | 3.98 | 0.65 | 0.91 | 0.95 | 7.29(d, J=9Hz, 2H) 6.88(d, J=9Hz, 2H) 5.04ᵇ(2H) 3.81(s, 3H) | 7.15(d, J=8.5Hz, 2H) 6.63(d, J=8.5Hz, 1H) 6.60(d, J=8.5Hz, 1H) 4.27(tq, J=7Hz, 6.5Hz, 2H) 3.75(dd, J=16Hz, 7Hz, 1H) 3.65(d, J=7Hz, 2H) 3.62(dd, J=16Hz, 7Hz, 1H) 3.47(s, 2H), 1.50(d, J=6.5Hz, 6H) | — |
| 12 | Cl | CH₃ |  | OH | H | OH | 4.72 | X | 4.00 | 0.68 | 0.91 | 0.98 | — | 7.14(d, J=8.5Hz, 2H) 6.63(d, J=8.5Hz, 1H) 6.59(d, J=8.5Hz, 1H) 4.27(tq, J=7Hz, 6.5Hz, 2H) 3.76(dd, J=16Hz, 7Hz, 1H) 3.65(d, J=7Hz, 2H) 3.62(dd, J=16Hz, 7Hz, 1H) 3.47(s, 2H), 1.50(d, J=6.5Hz, 6H) | 0.58, 0.60 |

TABLE 1-continued

| Example No. | X | $R_1$ | Y | $R_2$ | $R_3$ | $R_4$ | 3-H | 7-H | 12-H | 18-CH$_3$ | 19-CH$_3$ | 21-CH$_3^a$ | $R_4$ | $(X-CH-CH_2)_2-N-Y-COO-$ with $R_1$ | TLC $R_f$ Value |
|---|---|---|---|---|---|---|---|---|---|---|---|---|---|---|---|
| 13 | Cl | CH$_3$ | –CH$_2$–C$_6$H$_4$– | H | α-OH | –O–CH$_2$–C$_6$H$_4$–OCH$_3$ | 4.59 | 3.84 | X | 0.63 | 0.90 | 0.91 | 7.29(d, J=9Hz, 2H) 6.88(d, J=9Hz, 2H) 5.04$^b$(2H) 3.80(s, 3H) | 7.14(d, J=8.5Hz, 2H) 6.63(d, J=8.5Hz, H) 6.59(d, J=8.5Hz, 1H) 4.27(tq, J=7Hz, 6.5Hz, 2H) 3.76(dd, J=16Hz, 7Hz, 1H) 3.65(d, J=7Hz, 2H) 3.62(dd, J=16Hz, 7Hz, 1H) 3.46(s, 2H), 1.50(d, J=6.5Hz, 6H) | — |
| 14 | Cl | CH$_3$ | –CH$_2$–C$_6$H$_4$– | H | α-OH | OH | 4.58 | 3.86 | X | 0.66 | 0.91 | 0.94 | — | 7.14(d, J=8.5Hz, 2H) 6.62(d, J=8.5Hz, 1H) 6.59(d, J=8.5Hz, 1H) 4.27(tq, J=7Hz, 6.5Hz, 2H) 3.75(dd, J=16Hz, 7Hz, 1H) 3.65(d, J=7Hz) 3.61(dd, J=16Hz, 7Hz, 1H) 3.46(s, 2H), 1.50(d, J=6.5Hz, 6H) | 0.59, 0.61 |
| 15 | Cl | H | –(CH$_2$)$_2$–C$_6$H$_4$– | OH | H | –O–CH$_2$–C$_6$H$_4$–OCH$_3$ | 4.72 | X | 8.97 | 0.65 | 0.91 | 0.95 | 7.29(d, J=8.5Hz, 2H) 6.88(d, J=8.5Hz, 2H) 5.04$^b$(2H) 3.79(s, 3H) | 7.12~7.22(m, 1H) 6.48~6.63(m, 3H) 3.66$^c$(8H, max, 3.71, 3.68, 3.64, 3.62 2.88(t, J=8Hz, 2H) 2.57(t, J=8Hz, 2H) | — |
| 16 | Cl | H | –(CH$_2$)$_2$–C$_6$H$_4$– | OH | H | OH | 4.72 | X | 4.00 | 0.68 | 0.92 | 0.98 | — | 7.13~7.22(m, 1H) 6.50~6.66(m, 3H) 3.67$^c$(8H, max, 3.72, 3.69, 3.65, 3.63 2.89(t, J=8Hz, 2H) 2.57(t, J=8Hz, 2H) | 0.58 |
| 17 | Cl | H | –(CH$_2$)$_2$–C$_6$H$_4$– | OH | α-OH | NH–COOCH$_2$–C$_6$H$_5$ | 4.59 | 3.84 | 3.98 | 0.69 | 0.90 | 0.98 | 7.35(br, s, 5H), 6.11(br, t, J=5.5Hz, 1H) 5.18(s, 2H) 4.08(d, J=5.5Hz, 2H) | 7.13~7.21(m, 1H) 6.48~6.65(m, 3H) 3.67$^c$(8H, max, 3.72, 3.69, 3.65, 3.63 2.88(t, J=8Hz, 2H) 2.55(t, J=8Hz, 2H) | — |

TABLE 1-continued

| Example No. | X | R1 | Y | R2 | R3 | R4 | 3-H | 7-H | 12-H | 18-CH3 | 19-CH3 | 21-CH3 | R4[a] | R1 (X—CH—CH2)2—N—Y—COO— |
|---|---|---|---|---|---|---|---|---|---|---|---|---|---|---|
| 18 | Cl | H | —(CH2)2—⌬(CH3) | OH | α-OH | NH—CH2COOH | 4.57 | 3.85 | X | 0.66 | 0.88 | 0.97 | 3.99(br, s, 3H) | 7.12~7.22(m, 1H) 6.49~6.43(m, 3H) 3.66[c](8H, max, 3.71, 3.69, 3.64, 3.62) 2.87(t, J=8Hz, 2H) 2.55(t, J=8Hz, 2H) |
| 19 | Cl | H | —(CH2)2—⌬(CH3) | H | H | O—CH2—⌬ | 4.72 | X | X | 0.61 | 0.91 | 0.90 | 7.35(br, s, 5H) 5.09[b](2H) | 7.12~7.20(m, 1H) 6.48~6.65(m, 3H) 3.64[c](8H, max, 3.68, 3.66, 3.62, 3.59) 2.89(t, J=8Hz, 2H) 2.57(t, J=8Hz, 2H) |
| 20 | Cl | H | —(CH2)2—⌬(CH3) | H | H | OH | 4.73 | X | X | 0.64 | 0.92 | 0.91 | — | 7.12~7.20(m, 1H) 6.49~6.64(m, 3H) 3.66[c](8H, max, 3.71, 3.68, 3.64, 3.62) 2.89(t, J=8Hz, 2H) 2.58(t, J=8Hz, 2H) |
| 21 | Br | H | —(CH2)2—⌬(CH3) | H | β-OH | O—CH2—⌬—OCH3 | 4.68 | 3.57 | X | 0.65 | 0.95 | 0.91 | 7.29(d, J=8.5Hz, 2H) 6.88(d, J=8.5Hz, 2H) 5.04[b](2H) 3.80(s, 3H) | 7.13~7.21(m, 1H) 6.47~6.67(m, 3H) 3.76(t, J=7.5Hz, 4H) 3.45(t, J=7.5Hz, 4H) 2.90(t, J=8Hz, 2H) 2.58(t, J=8Hz, 2H) |
| 22 | Br | H | —(CH2)2—⌬(CH3) | H | β-OH | OH | 4.68 | 3.58 | X | 0.68 | 0.95 | 0.94 | — | 7.12~7.21(m, 1H) 6.47~6.67(m, 3H) 3.75(t, J=7.5Hz, 4H) 3.45(t, J=7.5Hz, 4H) 2.89(t, J=8Hz, 2H) 2.58(t, J=8Hz, 2H) |
| 23 | Br | H | —(CH2)2—⌬(CH3) | H | α-OH | O—CH2—⌬—OCH3 | 4.60 | 3.84 | X | 0.63 | 0.91 | 0.90 | 7.29(d, J=8.5Hz, 2H) 6.88(d, J=8.5Hz, 2H) 5.04[b](2H) 3.80(s, 3H) | 7.12~7.21(m, 1H) 6.46~6.65(m, 3H) 3.75(t, J=7.5Hz, 4H) 3.45(t, J=7.5Hz, 4H) 2.89(t, J=8Hz, 2H) 2.56(t, J=8Hz, 2H) |

TLC Rf Value: 18: 0.10; 19: —; 20: 0.68; 21: —; 22: 0.47; 23: —

TABLE 1-continued

| Example No. | X | R1 | Y | R2 | R3 | R4 | 3-H | 7-H | 12-H | 18-CH3 | 19-CH3 | 21-CH3 | R4 | $\overset{R_1}{\underset{}{(X-CH-CH_2)_2-N-Y-COO-}}$ | TLC Rf Value |
|---|---|---|---|---|---|---|---|---|---|---|---|---|---|---|---|
| 24 | Br | H | —(CH₂)₂— | H | α-OH | OH | 4.60 | 3.85 | X | 0.66 | 0.91 | 0.94 | — | 7.12~7.20(m, 1H) 6.45~6.66(m, 3H) 3.76(t, J=7.5Hz, 4H) 3.45(t, J=7.5Hz, 4H) 2.89(t, J=8Hz, 2H) 2.57(t, J=8Hz, 2H) | 0.60 |
| 25 | Cl | H | —(CH₂)₃— | H | α-OH | O—CH₂—⌬—OCH₃ | 4.59 | 3.85 | X | 0.63 | 0.91 | 0.90 | 7.29(d, J=8.5Hz, 2H) 6.88(d, J=8.5Hz, 2H) 5.04ᵇ(2H) 3.80(s, 3H) | 7.06(d, J=8.5Hz, 2H) 6.62(d, J=8.5Hz, 2H) 3.66ᶜ(8H, max, 3.69, 3.67, 3.64, 3.61) 2.54(t, J=7.5Hz, 2H) 2.27(t, J=7.5Hz, 2H) 1.89ᵈ | — |
| 26 | Cl | H | —(CH₂)₃— | H | α-OH | OH | 4.59 | 3.85 | X | 0.67 | 0.91 | 0.94 | — | 7.07(d, J=8.5Hz, 2H) 6.62(d, J=8.5Hz, 2H) 3.66ᶜ(8H, max, 3.70, 3.67, 3.64, 3.62) 2.57(t, J=7.5Hz, 2H) 2.27(t, J=7.5Hz, 2H) 1.91ᵈ | 0.62 |
| 27 | Cl | H | —(CH₂)₃— | OH | H | O—CH₂—⌬—OCH₃ | 4.72 | X | 3.96 | 0.65 | 0.91 | 0.95 | 7.28(d, J=8.5Hz, 2H) 6.88(d, J=8.5Hz, 2H) 5.04ᵇ(2H) 3.80(s, 3H) | 7.06(d, J=8.5Hz, 2H) 6.62(d, J=8.5Hz, 2H) 3.66ᶜ(8H, max, 3.69, 3.66, 3.63, 3.61) 2.54(t, J=7.5Hz, 2H) 2.26(t, J=7.5Hz, 2H) 1.92ᵈ | — |
| 28 | Cl | H | —(CH₂)₃— | OH | H | OH | 4.72 | X | 4.00 | 0.68 | 0.92 | 0.98 | — | 7.07(d, J=8.5Hz, 2H) 6.63(d, J=8.5Hz, 2H) 3.65ᶜ(8H, max, 3.70, 3.67, 3.64, 3.62) 2.55(t, J=7.5Hz, 2H) 2.26(t, J=7.5Hz, 2H) 1.89ᵈ | 0.60 |
| 29 | Cl | H | —(CH₂)₃— | OH | H | NH—CH₂COOH | 4.90 | X | 4.16 | 0.71 | 0.90 | 1.16 | 8.92(t, J=5.5Hz, 1H) 4.51(d, J=5.5Hz, 2H) | 7.18(d, J=8.5Hz, 2H) 6.78(d, J=8.5Hz, 2H) 3.72(br, s, 8H) 2.63(t, J=7.5Hz, 2H) 2.41(t, J=7.5Hz, 2H) 2.02ᵈ | 0.21 |

TABLE 1-continued

| Example No. | X | R₁ | Y | R₂ | R₃ | R₄ | 3-H | 7-H | 12-H | 18-CH₃ | 19-CH₃ | 21-CH₃ | R₄ | $R_1$ $(X-CH-CH_2)_2-N-Y-COO-$ | TLC $R_f$ Value |
|---|---|---|---|---|---|---|---|---|---|---|---|---|---|---|---|
| 30 | Cl | H | —CH₂— | OH | α-OH | O—CH₂——OCH₃ | 4.81 | 3.87 | 4.00 | 0.68 | 0.93 | 0.96 | 7.29(d, J=8.5Hz, 2H) 6.88(d, J=8.5Hz, 2H) 5.04ᵇ(2H) 3.80(s, 3H) | 7.98(d, J=8.5Hz, 2H) 7.40(d, J=8.5Hz, 2H) 3.79(s, 2H) 3.50(t, J=7Hz, 4H) 2.92(t, J=7Hz, 4H) | — |
| 31 | Cl | H | —CH₂— | OH | α-OH | OH | 4.82 | 3.90 | 4.02 | 0.70 | 0.91 | 0.98 | — | 7.99(d, J=8.5Hz, 2H) 7.41(d, J=8.5Hz, 2H) 3.80(s, 2H) 3.50(t, J=7Hz, 4H) 2.92(t, J=7Hz, 4H) | 0.41 |
| 32 | Cl | H | —CH₂— | H | β-OH | O—CH₂——OCH₃ | 4.91 | X | X | 0.66 | 0.98 | 0.91 | 7.29(d, J=8.5Hz, 2H) 6.88(d, J=8.5Hz, 2H) 5.04ᵇ(2H) 3.80(s, 3H) | 7.99(d, J=8.5Hz, 2H) 7.42(d, J=8.5Hz, 2H) 3.79(s, 2H) 3.50(t, J=7Hz, 5H) 2.92(t, J=7Hz, 4H) | — |
| 33 | Cl | H | —CH₂— | H | β-OH | OH | 4.92 | X | X | 0.69 | 0.99 | 0.94 | — | 7.99(d, J=8.5Hz, 2H) 7.42(d, J=8.5Hz, 2H) 3.80(s, 2H) 3.50(t, J=7Hz, 5H) 2.93(t, J=7Hz, 4H) | 0.44 |
| 34 | Cl | H | —CH₂— | H | α-OH | O—CH₂——OCH₃ | 4.62 | 3.84 | X | 0.63 | 0.90 | 0.91 | 7.29(d, J=8.5Hz, 2H) 6.88(d, J=8.5Hz, 2H) 5.04ᵇ(2H) 3.80(s, 3H) | 3.52(t, J=7Hz, 4H) 3.46(s, 2H) 3.07(t, J=7Hz, 4H) | — |
| 35 | Cl | H | —CH₂— | H | α-OH | OH | 4.62 | X | X | 0.66 | 0.91 | 0.94 | — | 3.52(t, J=7Hz, 4H) 3.47(s, 2H) 3.07(t, J=7Hz, 4H) | 0.54 |
| 36 | Cl | H | —CH₂— | OH | H | O—CH₂— | 4.76 | 3.98 | X | 0.66 | 0.92 | 0.96 | 7.35(br, s, 5H) 5.11ᵇ(2H) | 3.52(t, J=7Hz, 4H) 3.47(s, 2H) 3.07(t, J=7Hz, 4H) | — |
| 37 | Cl | H | —CH₂— | OH | H | OH | 4.76 | X | 4.01 | 0.69 | 0.92 | 0.99 | — | 3.52(t, J=7Hz, 4H) 3.47(s, 2H) 3.07(t, J=7Hz, 4H) | 0.52 |

TABLE 1-continued

| Example No. | X | R$_1$ | Y | R$_2$ | R$_3$ | R$_4$ | 3-H | 7-H | 12-H | 18-CH$_3$ | 19-CH$_3$ | 21-CH$_3$[a] | R$_4$ | $\overset{R_1}{\underset{|}{(X-CH-CH_2)_2-N-Y-COO-}}$ | TLC R$_f$ Value |
|---|---|---|---|---|---|---|---|---|---|---|---|---|---|---|---|
| 38 | Cl | H | —CH$_2$— | OH | α-OH | OH | 4.62 | 3.87 | 4.00 | 0.70 | 0.91 | 0.99 | — | 3.52(t, J=7Hz, 4H) 3.48(s, 2H) 3.08(t, J=7Hz, 4H) | 0.39 |
| 39 | Cl | H | —CH$_2$— | OH | α-OH | NH—CH$_2$COO—CH$_2$—⌬ | 4.62 | 3.84 | 3.98 | 0.71 | 0.93 | 0.98 | 7.35(br, s, 5H) 6.44(br, t, 1H) 5.18(s, 2H) 4.08(d, J=5.5Hz, 2H) | 3.52(t, J=7Hz, 4H) 3.47(s, 2H) 3.07(t, J=7Hz, 4H) | — |
| 40 | Cl | H | —CH$_2$— | OH | α-OH | NH—CH$_2$—COOH | 4.79 | 4.05 | 4.23 | 0.78 | 0.95 | 1.20 | 8.93(t, J=5.5Hz, 1H) 4.50(t, J=5.5Hz, 2H) | 3.65(t, J=7Hz, 4H) 3.58(s, 2H) 3.15(t, J=7Hz, 4H) | 0.09 |
| 41 | Cl | H | —CH$_2$— | H | β-OH | OH | 4.71 | X | X | 0.68 | 0.96 | 0.94 | — | 3.53(t, J=7Hz, 5H) 3.49(s, 2H) 3.08(t, J=7Hz, 4H) | 0.42 |
| 42 | Cl | CH$_3$ | —CH$_2$— | H | β-OH | OH | 4.71 | 3.57 | X | 0.68 | 0.96 | 0.94 | — | 3.92~4.05(m, 2H) 3.50(s, 1H) 3.48(s, 1H) 2.82~3.07(m, 4H) 1.51(d, J=6.5Hz, 6H) | 0.41, 0.43 |
| 43 | Cl | H | —(CH$_2$)$_3$— | OH | H | O—CH$_2$—⌬—OCH$_3$ | 4.72 | X | 3.97 | 0.65 | 0.92 | 0.95 | 7.29(d, J=8.5Hz, 2H) 6.88(d, J=8.5Hz, 2H) 5.04[b](2H) 3.81(s, 3H) | 3.50(t, J=7Hz, 4H) 2.87(t, J=7Hz, 4H) 2.60(t, J=7Hz, 2H) 2.33(t, J=7Hz, 2H) 1.75[d] | — |
| 44 | Cl | H | —(CH$_2$)$_3$— | OH | H | OH | 4.72 | X | 4.00 | 0.67 | 0.92 | 0.99 | — | 3.50(t, J=7Hz, 4H) 2.87(t, J=7Hz, 4H) 2.60(t, J=7Hz, 2H) 2.33(t, J=7Hz, 2H) 1.76[d] | 0.36 |

TABLE 1-continued

| Example No. | X | R₁ | Y | R₂ | R₃ | R₄ | 3-H | 7-H | 12-H | 18-CH₃ | 19-CH₃ | 21-CH₃ | R₄ | $R_1$ $\|$ $(X-CH-CH_2)_2-N-Y-COO-$ | TLC $R_f$ Value |
|---|---|---|---|---|---|---|---|---|---|---|---|---|---|---|---|
| 45 | Cl | H | —(CH₂)₃— | H | α-OH | O—CH₂—⟨⟩—OCH₃ | 4.59 | 3.84 | X | 0.63 | 0.91 | 0.91 | 7.29(d, J=8.5Hz, 2H) 6.88(d, J=8.5Hz, 2H) 5.04ᵇ(2H) 3.80(s, 3H) | 3.94(t, J=7Hz, 4H) 2.85(t, J=7Hz, 4H) 2.58(t, J=7Hz, 2H) 2.31(t, J=7Hz, 2H) 1.75ᵈ | — |
| 46 | Cl | H | —(CH₂)₃— | H | α-OH | OH | 4.59 | 3.86 | X | 0.67 | 0.92 | 0.94 | — | 3.50(t, J=7Hz, 4H) 2.87(t, J=7Hz, 4H) 2.59(t, J=7Hz, 2H) 2.32(t, J=7Hz, 2H) 1.75ᵈ | 0.38 |
| 47 | Cl | H | —(CH₂)₅— | OH | α-OH | O—CH₂—⟨⟩—OCH₃ | 4.57 | 3.86 | 3.97 | 0.68 | 0.92 | 0.96 | 7.29(d, J=8.5Hz, 2H) 6.88(d, J=8.5Hz, 2H) 5.04ᵇ(2H) 3.80(s, 3H) | 3.49(t, J=7Hz, 4H) 2.85(t, J=7Hz, 4H) 2.54(t, J=7Hz, 2H) 2.28(t, J=7Hz, 2H) | — |
| 48 | Cl | H | —(CH₂)₅— | OH | α-OH | OH | 4.58 | 3.88 | 4.01 | 0.70 | 0.91 | 0.99 | — | 3.50(t, J=7Hz, 4H) 2.87(t, J=7Hz, 4H) 2.56(t, J=7Hz, 2H) 2.27(t, J=7Hz, 2H) | 0.31 |
| 49 | Cl | H | —(CH₂)₅— | H | β-OH | O—CH₂—⟨⟩—OCH₃ | 4.69 | 3.58 | X | 0.64 | 0.96 | 0.93 | 7.30(d, J=8.5Hz, 2H) 6.88(d, J=8.5Hz, 2H) 5.04ᵇ(2H) 3.81(s, 3H) | 3.50(t, J=7Hz, 4H) 2.86(t, J=7Hz, 4H) 2.55(t, J=7Hz, 2H) 2.28(t, J=7Hz, 2H) | — |
| 50 | Cl | H | —(CH₂)₅— | H | β-OH | OH | 4.68 | 3.58 | X | 0.68 | 0.96 | 0.94 | — | 3.50(t, J=7Hz, 4H) 2.87(t, J=7Hz, 4H) 2.56(t, J=7Hz, 2H) 2.28(t, J=7Hz, 2H) | 0.31 |
| 51 | Cl | H | ⟨⟩—CH₂— | H | β-OH | NH—(CH₂)₂—SO₃H | 4.92 | X | X | 0.66 | 0.91 | 0.96 | 4.22(br, t, 2H) 3.54(br, t, 2H) | 7.43(d, J=8.5Hz, 2H) 6.83(d, J=8.5Hz, 2H) 3.80(s, 2H) 3.71(br, s, 8H) | — |

TABLE 1-continued

| Example No. | X | R₁ | Y | R₂ | R₃ | R₄ | 3-H | 7-H | 12-H | 18-CH₃ | 19-CH₃ | 21-CH₃ | R₄ (NMR) | $R_1$<br>(X—CH—CH₂)₂—N—Y—COO— | TLC Rf Value |
|---|---|---|---|---|---|---|---|---|---|---|---|---|---|---|---|
| 52 | Cl | H | —COO—C₆H₄— | OH | α-OH | —OCH₂—C₆H₄—OCH₃ | 4.81 | X | 3.99 | 0.67 | 0.92 | 0.95 | 7.29(d, J=8.5Hz, 2H) 6.87(d, J=8.5Hz, 2H) 5.04ᵇ(2H) 3.79(s, 3H) | 8.04(d, J=8.5Hz, 2H) 7.18(d, J=8.5Hz, 2H) 3.83~3.93(m, 3H) 3.68~3.83(m, 6H) | — |
| 53 | Cl | H | —COO—C₆H₄— | OH | α-OH | OH | 4.80 | X | 4.00 | 0.67 | 0.91 | 0.95 | — | 8.05(d, J=8.5Hz, 2H) 7.18(d, J=8.5Hz, 2H) 3.82~3.91(m, 3H) 3.69~3.82(m, 6H) | 0.39 |
| 54 | Cl | H | —COO—C₆H₄—CH₂— | OH | α-OH | —OCH₂—C₆H₅ | 4.56 | X | 3.96 | 0.67 | 0.90 | 0.97 | 7.35(br, s, 5H) 5.11ᵇ(2H) | 7.29(d, J=8.5Hz, 2H) 7.05(d, J=8.5Hz, 2H) 3.80~3.90(m, 3H) 3.69~3.90(m, 6H) 3.55(s, 2H) | — |
| 55 | Cl | H | —COO—C₆H₄—CH₂— | OH | α-OH | OH | 4.57 | X | 3.98 | 0.69 | 0.89 | 0.98 | — | 7.28(d, J=8.5Hz, 2H) 7.06(d, J=8.5Hz, 2H) 3.80~3.91(m, 3H) 3.69~3.81(m, 6H) 3.55(s, 2H) | 0.37 |
| 56 | Cl | H | —CH₂— | H | β-OH | NH(CH₂)₂SO₃H | 4.90 | X | X | 0.65 | 0.92 | 0.96 | 8.60(br, t, 1H) 4.24~4.36 (m, 2H) 3.57(t, J=7Hz, 2H) | 3.81(s, 2H) 3.75(t, J=7.5Hz, 4H) 3.27(t, J=7.5Hz, 4H) | — |

Remarks:
(1) The measurement of ¹H—NMR was carried out in pyridine-d₅ for the compounds obtained in Examples 29, 40, 51 and 56, and in chloroform-d₁ for the compounds obtained in the remaining Examples.
The mark X indicates "undetectable because of overlapping with other signals".
ᵃd, J=6Hz;
ᵇsplit into AB pattern, showing the center value;
ᶜsplit into A₂B₂ pattern, showing the center value;
ᵈthe coupling constant being undetectable because of overlapping with other signals, only the center value is shown.
(2) The thin-layer chromatography was conducted by using TLC glass plate 60F₂₅₄ (Merck & Co., Inc.) on which the test compounds were developed by 15 cm with a 10:5:1 benzene-ethyl acetate-acetic acid mixture, sprayed with conc. sulfuric acid and then heated for color development.

Utility

The bile acid derivatives according to the present invention have carcinostatic activity and yet are of low toxicity.

Accordingly, these compounds can be used as carcinostatic agents (for details, see the description given hereinafter).

Production of the bile acid derivatives

The bile acid derivatives of the formula (I) according to the present invention can be produced by any desired method suited for the purpose. Preferred method:

Preferable examples of such method comprise practicing the step (a) and, if necessary, up to the step (b) or (c) as described above.

Step (a)

For example, an alkali salt of a natural bile acid selected from cholic acid, deoxycholic acid, ursodeoxycholic acid, chenodeoxycholic acid and lithocholic acid is allowed to react with a lower alkyl halide having 1 to 4 carbon atoms such as methyl iodide, methyl bromide, methyl chloride, ethyl iodide, ethyl bromide, isopropyl iodide or butyl bromide, or a benzyl halide such as benzyl chloride, benzyl bromide or p-methoxybenzyl chloride, or an m- or p-substituted lower alkoxybenzyl halide in a conventional manner, and the alkyl ester of bile acid obtained (the compound of the above formula (II) wherein $R_4'$ is a lower alkoxyl group, benzyloxyl group or m- or p-lower alkoxybenzyloxyl group) is used as the starting reactant. This reactant is allowed to react with a compound of the formula (III), whereby the compound of the formula (I) wherein $R_4$ is a lower alkoxyl group or a benzyloxyl group or m- or p-lower alkoxybenzyloxyl group of the formula

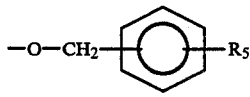

(wherein $R_5$ is as defined previously, can be obtained.

The "m- or p-lower alkoxybenzyloxyl group" herein refers to a substituent having a lower alkoxyl group with 1 to 4 carbon atoms at the m- or p-position of the benzyloxyl group. One example of such substituents is a p-methoxybenzyloxyl group shown in Examples which will be described hereinlater.

Further, the compound of the formula (III) can be easily prepared in accordance with any known method (J. Chem. Soc., 2386 (1953)).

In the step (a), any reaction conditions suited for the purpose can be employed. For example, the compound of the formula (II) can be reacted with the compound of the formula (III) in the presence of any condensing agent capable of condensing a carboxyl group and a hydroxyl group (e.g., N,N'-dicyclohexylcarbodiimide, N,N'-diethylcarbodiimide, 1-ethyl-3-(3-dimethylaminopropyl)carbodiimidehydrochloride, 1-ethoxycarbonyl-2-ethoxy-1,2-dihydroquinoline, and N,N'-disuccinimidyl carbonate). Alternatively, the compound of the formula (III) can be converted beforehand into a reactive acid derivative such as an acid halide, acid anhydride, acid anhydride mixture or active ester thereof by oxalyl chloride, thionyl chloride, thionyl bromide, dicyclohexylcarbodiimide, N,N'-disuccinimidyl carbonate, and ethyl chlorocarbonate, and then reacted with the compound of the formula (II).

In order to facilitate the above reaction, bases, such as sodium carbonate, potassium carbonate, sodium hydrogencarbonate and like inorganic salts or pyridine, triethylamine and like tertiary amines, may be added.

Preferably, this step (a) is carried out in a solvent. The solvents for use in the reaction may be those which have no reactive hydrogen atom, i.e., aprotic solvents. For example, dichloromethane, chloroform, ethyl acetate, benzene, acetone, N,N-dimethylformamide, and dimethyl sulfoxide can be used as a solvent.

In the reaction in the step (a) set forth above, the reactivity of the respective hydroxyl groups of the bile acid ester is in the order of 3-position > 7-position ≧ 12-position. By increasing the quantity of the compound of the formula (III) fed to the reaction system, disubstituted and trisubstituted compounds can be obtained. If an appropriate quantity of the compound (III) is selected according to the reaction conditions, a 3-substituted compound can be obtained preferentially.

Step (b)

The compound of the formula (I) obtained in the preceding step (a) wherein $R_4$ is a lower alkoxyl group, or benzyloxyl group or m- or p-lower alkoxybenzyloxyl group is subjected to catalytic reduction or to acid treatment, whereby the compound of the formula (I) wherein $R_4$ is a hydroxyl group can be obtained.

The catalytic reduction is carried out ordinarily in an organic solvent such as tetrahydrofuran, ethyl acetate or a lower alcohol or a solution mixture of two or more thereof in a hydrogen atmosphere in the presence of a catalyst for hydrogenation such as palladium or platinum.

In the case of the acid treatment, the compound is ordinarily brought into contact with a strongly acidic atmosphere such as trifluoroacetic acid-anisole or hydrobromic acid-acetic acid.

Step (c)

The compound of the formula (I) obtained in the preceding step (b) wherein $R_4$ is a hydroxyl group is reacted with a compound of the formula (IV) in the presence of a condensing agent in an aprotic solvent similarly as in the step (a), whereby the compound of the formula (I) wherein $R_4$ is $-NH-(CH_2)_m-R_6$ can be obtained. The condensing agent herein refers to any condensing agent capable of causing condensation of a carboxyl group and an amino group, such as N,N'-dicyclohexylcarbodiimide, hydrochloric acid 1-ethyl-3-(3-dimethylaminopropyl)carbodiimide hydrochloride, 1-ethoxycarbonyl-2-ethoxy-1,2-dihydroquinoline or N,N'-disuccinimidyl carbonate.

Other methods

The bile acid derivatives of the present invention can also be produced by methods other than that described above. Examples of such methods are as follows.

The compound of the formula (I) wherein Y is $-CH_2-$ may be produced advantageously by the following method.

A bile acid selected from cholic acid, deoxycholic acid, ursodeoxycholic acid, chenodeoxycholic acid and lithocholic acid or a benzyl or p-methoxybenzyl ester thereof is allowed to react with a monohaloacetic acid in the presence of a condensing agent or with a reactive acid derivative thereof, whereby a bile acid derivative having a haloacetylated hydroxyl group at its 3-position can be obtained. The definitions of the condensing agent and reactive acid derivative as well as the reaction conditions required are as described in detail in the above step (a).

Subsequently, the compound having a haloacetyl group is allowed to react with a compound of the formula (V):

wherein X is a halogen atom and $R_1$ is a hydrogen atom or a lower alkyl group, and, if necessary, further to undergo the steps (b) and (c) as set forth above, whereby the compound of the formula (I wherein Y is $-CH_2-$ can be obtained.

Further, the compound of the formula (I) wherein $R_4$ is $-NH-CH_2-COOH$ or $NH-CH_2-COOCH_2Ph$ can be produced by substantially the same procedures as the aforementioned steps (a) and (b) from a benzyl ester of a bile acid conjugated with glycine.

Use of compound/carcinostatic agent

As is apparent from the Experimental example set forth hereinafter, the bile acid derivatives according to the present invention have carcinostatic activity and yet are of low toxicity, and therefore these compounds can be useful as carcinostatic agents.

That is, the carcinostatic agent as an embodiment of the present invention comprises a bile acid derivative represented by the above formula (I) or its salt as the active ingredient.

The carcinostatic agent comprises any of the above bile acid derivatives alone or a mixture thereof or a mixture thereof with a liquid or solid auxiliary component in preparation such as an excipient, binder or diluent, which agent can be administered orally or parenterally in any desired preparation form such as powder, granule, tablet, capsule, or injection.

Furthermore, if desired, it can also be formulated with any other carcinostatic agents (e.g., 5-FU, mitomycin or crestin). The dose, which may be suitably increased or decreased depending on the age, the body weight or the condition of disease, is ordinarily and desirably 10 mg to 10 g as the bile acid derivative or its salt for oral administration for a human adult per day. A preferable example comprises the bile acid derivative and an auxiliary component in preparation. Another preferable example of the present invention is in a unit dosage form for one administration or several divided administrations of the above dose per day.

EXAMPLES

Synthesis of compound

In order to indicate more fully the nature and utility of this invention, the following specific examples of practice are set forth, it being understood that these examples are presented as illustrative only and not intended to limit the scope of the invention.

In the Examples relating to the synthesis of compounds, the end products were obtained as colorless powder unless otherwise indicated. The data on the $^1$H-NMR spectra of the compounds thus obtained are shown in Table 1.

EXAMPLE 1 p-Methoxybenzyl 3-O-[p-[N,N-bis(2-chloroethyl)amino]-phenylacetyl] cholate 2.8 g of p-[N,N-bis(2-chloroethyl)amino]phenylacetic acid was added to 10 ml of dichloromethane containing 1.4 g of oxalyl chloride dissolved therein, and the mixture was stirred for 1 hour at room temperature to obtain a suspension of a hydrochloride of the corresponding acid chloride.

5.3 g of p-methoxybenzyl cholate and 1.6 g of pyridine were dissolved in 20 ml of dichloromethane, and the solution was ice-cooled. To this solution was added the suspension obtained above with stirring, and the resulting mixture was allowed to react for 30 minutes at room temperature. To the reaction mixture was then added 100 ml of chloroform. The chloroform solution was washed with water and a 2% aqueous sodium carbonate solution. The resultant solution was dried over anhydrous magnesium sulfate, and the solvent was distilled off. The residue obtained was purified by silica gel column chromatography and evaporated to dryness under reduced pressure to obtain 3.6 g of the title compound (yield 46%).

EXAMPLE 2

3-O-[p-(N,N-bis(2-chloroethyl)amino)phenylacetyl] cholic acid

To 2.2 g of the compound obtained in Example 1 were added 1.5 ml of anisole and 4.5 g of trifluoroacetic acid, and the mixture was left standing for 10 minutes at room temperature. To the resultant mixture were added 30 ml of chloroform and 30 ml of water. Thereafter, sodium hydrogencarbonate was added to neutralize the aqueous layer. The aqueous layer was separated, and the chloroform layer was dried over anhydrous magnesium sulfate, and the solvent was distilled off. The residue obtained was purified by silica gel column chromatography to obtain 1.5 g of the title compound (yield 80%), which was found, when recrystallized from acetonitrile, to have a melting point of 114 to 116° C.

EXAMPLE 3

Benzyl 3-O-[p-(N,N-bis(2-chloroethyl)amino)phenylacetyl]-chenodeoxycholate 480 mg of benzyl chenodeoxycholate was reacted similarly as in Example 1 on a scale of 1/10 to obtain 260 mg of the title compound (yield 35%).

EXAMPLE 4

3-O-[p-(N,N-bis(2-chloroethyl)amino)phenylacetyl]-chenodeoxycholic acid 200 mg of the compound obtained in Example 3 was hydrogenated in a solution mixture of 2 ml of isopropyl alcohol and 5 ml of ethyl acetate in the presence of 60 mg of 5% palladium carbon. The catalyst was then filtered off, and the filtrate was distilled and evaporated to dryness under reduced pressure to obtain 170 mg of the title compound (yield 97%).

EXAMPLE 5 p-Methoxybenzyl
3-O-[p-(N,N-bis(2-chloroethyl)amino)phenylacetyl]ursodeoxycholate 4.8 g of p-[N,N-bis(2-chloroethyl)amino]phenylacetic acid, 3.3 g of 1-ethyl-3-(3-dimethylaminopropyl)carbodiimide hydrochloride, 1.1 g of triethylamine and 5.2 g of ursodeoxycholic acid were added to 50 ml of dichloromethane. The mixture was stirred for 16 hours at room temperature and thereafter treated similarly as in Example 1 to obtain 4.5 g of the title compound (yield 58%).

EXAMPLE 6

3-O-[p-N,N-bis(2-chloroethyl)amino)phenylacetyl]ursodeoxycholic acid 2.3 g of the compound obtained in Example 5 was reacted similarly as in Example 2 to obtain 1.6 g of the title compound (yield 82%).

EXAMPLE 7 p-Methoxybenzyl
3-O-[p-(N,N-bis(2-bromoethyl)amino)phenylacetyl] cholate 370 mg of p-[N,N-bis(2-bromoethyl)amino]phenylacetic acid and 530 mg of p-methoxybenzyl cholate were subjected to a reaction similarly as in Example 3 (in this case, the acid chloride did not form a suspension but formed a homogeneous solution) to obtain 260 mg of the title compound (yield 30%).

EXAMPLE 8

3-O-[p-(N,N-bis(2-bromoethyl)amino)phenylacetyl] cholic acid 200 mg of the compound obtained in Example 7 was reacted similarly as in Example 2 on a scale of 1/10 to obtain 130 mg of the title compound (yield 75%).

EXAMPLE 9 p-Methoxybenzyl
3-O-[p-(N,N-bis(2-bromoethyl)amino)phenylacetyl] deoxycholate 520 mg of p-methoxybenzyl deoxycholate was reacted similarly as in Example 7 to obtain 275 mg of the title compound (yield 32%).

EXAMPLE 10

3-O-[p-(N,N-bis(2-bromoethyl)amino)phenylacetyl]-deoxycholic acid 200 mg of the compound obtained in Example 9 was reacted similarly as in Example 8 to obtain 155 mg of the title compound (yield 90%).

EXAMPLE 11 p-Methoxybenzyl
3-O-[p-(N,N-bis(2-chloro-n-propyl)amino)phenylacetyl] deoxycholate 310 mg of p-N,N-bis (2-chloro-n-propyl)amino]-phenylacetic acid (an equivalent mixture of a racemic modification and a meso modification) and 520 mg of p-methoxybenzyl deoxycholate were subjected to a reaction similarly as in Example 7 to obtain 170 mg of the title compound (yield 21%).

EXAMPLE 12

3-O-[p-(N,N-bis(2-chloro-n-propyl)amino)-phenylacetyl]deoxycholic acid 100 mg of the compound obtained in Example 11 was reacted similarly as in Example 8 to obtain 70 mg of the title compond (yield 80%).

EXAMPLE 13 p-Methoxybenzyl
3-O-[p-(N,N-bis(2-chloro-n-propyl)amino)phenylacetyl] chenodeoxycholate 520 mg of p-methoxybenzyl chenodeoxycholate was reacted similarly as in Example 11 to obtain 120 mg of the title compound (yield 15%).

EXAMPLE 14

3-O-[p-(N,N-bis(2-chloro-n-propyl)amino)-phenylacetyl]chenodeoxycholic acid 100 mg of the compound obtained in Example 13 was reacted similarly as in Example 8 to obtain 75 mg of the title compound (yield 89%).

EXAMPLE 15 p-Methoxybenzyl
3-O-[3-(m-(N,N-bis(2-chloroethyl)amino)phenyl)propionyl] deoxycholate 300 mg of 3-[m-(N,N-bis(2-chloroethyl)amino)phenyl] propionic acid and 520 mg of p-methoxybenzyl deoxycholate were subjected to a reaction similarly as in Example 7 to obtain 290 mg of the title compound (yield 36%).

EXAMPLE 16

3-O[3-(m-(N,N-bis(2-chloroethyl)amino)phenyl)propionyl]deoxycholic acid 200 mg of the compound obtained in Example 15 was reacted similarly as in Example 8 to obtain 155 mg of the title compound (yield 91%).

EXAMPLE 17

Benzyl
3-O-[3-(m-(N,N-bis(2-chloroethyl)amino)phenyl)propionyl] glycocholate 560 mg of benzyl glycocholate was reacted similarly as in Example 15 to obtain 340 mg of the title compound (yield 41%).

EXAMPLE 18

3-O-[3-(m-(N,N-bis(2-chloroethyl)amino)phenyl)propionyl] glycocholic acid 200 mg of the compund obtained in Example 17 was hydrogenated in a solution mixture of 2 ml of methanol and 10 ml of ethyl acetate in the presence of 100 mg of 5% palladium carbon. The catalyst was then filtered off, and the filtrate was distilled and evaporated to dryness under reduced pressure to obtain 170 mg of the title compound (yield 96%).

EXAMPLE 19

Benzyl 3-O-[3-(m-(N,N-bis(2-chloroethyl)amino)phenyl)propionyl] lithocholate 470 mg of benzyl lithocholate was reacted similarly as in Example 15 to obtain 470 mg of the title compound (yield 63%).

EXAMPLE 20

3-O-[3-(m-(N,N-bis(2-chloroethyl)amino)phenyl)propionyl] lithocholic acid 200 mg of the compound obtained in Example 19 was reacted similarly as in Example 18 to obtain 160 mg of the title compound (yield 92%).

EXAMPLE 21 p-Methoxybenzyl 3-O-[3-(m-(N,N-bis(2-bromoethyl)amino)phenyl)propionyl] ursodeoxycholate 380 mg of 3-[m-(N,N-bis(2-bromoethyl)amino)phenyl] propionic acid and 520 mg of p-methoxybenzyl ursodeoxycholate were subjected to a reaction similarly as in Example 7 to obtain 365 mg of the title compound (yield 41%).

EXAMPLE 22

3-O-[3-(m-(N,N-bis(2-bromoethyl)amino)phenyl)propionyl] ursodeoxycholic acid 200 mg of the compound obtained in Example 21 was reacted similarly as in Example 8 to obtain 96 mg of the title compound (yield 56%).

EXAMPLE 23 p-Methoxybenzyl 3-O-[3-(m-(N,N-bis(2-bromoethyl)amino)phenyl)propionyl] chenodeoxycholate 520 mg of p-methoxybenzyl chenodeoxycholate was reacted similarly as in Example 21 to obtain 310 mg of the title compound (yield 35%).

EXAMPLE 24

3-O-[3-(m-(N,N-bis(2-bromoethyl)amino)phenyl)propionyl] chenodeoxycholic acid 200 mg of the compound obtained in Example 24 was reacted similarly as in Example 8 to obtain 130 mg of the title compound (yield 74%).

EXAMPLE 25 p-Methoxybenzyl 3-O-[4-(p-(N,N-bis(2-chloroethyl)amino)phenyl)butyryl] chenodeoxycholate 310 mg of chlorambucil and 520 mg of p-methoxybenzyl chenodeoxycholate were subjected to a reaction similarly as in Example 7 to obtain 210 mg of the title compound (yield 26%).

EXAMPLE 26

3-O-[4-(p-(N,N-bis(2-chloroethyl)amino)phenyl)butyryl] chenodeoxycholic acid 150 mg of the compound obtained in Example 25 was reacted similarly as in Example 18. The product was purified by silica gel column chromatography and evaporated to dryness under reduced pressure to obtain 75 mg of the title compound (yield 59%).

EXAMPLE 27 p-Methoxybenzyl 3-O-[4-(p-(N,N-bis(2-chloroethyl)amino)phenyl)butyryl] deoxycholate 520 mg of p-methoxybenzyl deoxycholate was reacted similarly as in Example 25 to obtain 290 mg of the title compound (yield 36%).

EXAMPLE 28

3-O-[4-(p-(N,N-bis(2-chloroethyl)amino)phenyl)butyryl] deoxycholic acid 200 mg of the compound obtained in Example 27 was reacted similarly as in Example 8 to obtain 98 mg of the title compound (yield 56%).

EXAMPLE 29

3-O-[4-(p-(N,N-bis(2-chloroethyl)amino)phenyl)butyryl] glycodeoxycholic acid 90 mg of the compound obtained in Example 28, 15 mg of glycine, 50 mg of 1-ethoxycarbonyl-2-ethoxy-1,2-dihydroquinoline, and 25 mg of triethylamine were added to 2 ml of DMF, and the mixture was stirred for 1 hour at 80° C. The reaction solution was added to 50 ml of diisopropyl ether, and the mixture was left standing overnight. The precipitate formed was dissolved in 50 ml of ethyl acetate, washed with 0.2 N hydrochloric acid, and thereafter dried over anhydrous sodium sulfate, and the solvent was distilled off. The residue was purified by silica gel column chromatography to obtain 35 mg of the title compound (yield 36%).

EXAMPLE 30 p-Methoxybenzyl 3-O-[p-(N,N-bis(2-chloroethyl)aminomethyl)benzoyl] cholate 280 mg of p-[N,N-bis(2-chloroethyl)aminomethyl] benzoic acid and 530 mg of p-methoxybenzyl cholate were reacted similarly as in Example 7 to obtain 150 mg of the title compound (yield 18%).

EXAMPLE 31

3-O-[p-(N,N-bis(2-chloroethyl)aminomethyl)benzoyl] cholic acid 100 mg of the compound obtained in Example 30 was reacted similarly as in Example 8 to obtain 60 mg of the title compound (yield 71%).

EXAMPLE 32 p-Methoxybenzyl 3-O-[p-(N,N-bis(2-chloroethyl)amino-methyl)benzoyl] ursodeoxycholate 280 mg of p-[N,N-bis(2-chloroethyl)aminomethyl] benzoic acid was heated under reflux for 5 hours in 1 ml of thionyl chloride which was then distilled off under reduced pressure. The residue was dissolved in 4 ml of dichloromethane, and the solution plus 520 mg of p-methoxybenzyl ursodeoxycholate were reacted similarly as in Example 7 to obtain 180 mg of the title compound (yield 23%).

EXAMPLE 33

3O-[p-(N,N-bis(2-chloroethyl)aminomethyl)benzoyl]ursodeoxycholic acid 100 mg of the compound obtained in Example 32 was reacted similarly as in Example 8 to obtain 70 mg of the title compound (yield 83%).

EXAMPLE 34 p-Methoxybenzyl 3-O-[N,N-bis(2-chloroethyl)aminoacetyl]chenodeoxycholate 0.5 g of N,N-bis(2-chloroethyl) glycine, 1.05 g of p-methoxybenzyl chenodeoxycholate, 0.6 g of dicyclohexylcarbodiimide, and 0.3 g of N-methylimidazole were added to 5 ml of dichloromethane, and the mixture was stirred for 20 hours at room temperature.

The crystal thus precipitated was filtered off, and 100 ml of chloroform was added to the filtrate. The mixture was washed with 1% sodium hydrogencarbonate solution, and then dried over anhydrous magnesium sulfate, and thereafter the solvent was distilled off. The residue was purified by silica gel chromatography to obtain 320 mg of the title compound (yield 22%).

EXAMPLE 35

3-O-[N,N-bis(2-chloroethyl)aminoacetyl] chenodeoxycholic acid 200 mg of the compound obtained in Example 34 was reacted similarly as in Example 8 to obtain 155 mg of the title compound (yield 94%).

EXAMPLE 36

Benzyl 3-O-[N,N-bis(2-chloroethyl)aminoacetyl] deoxycholate 5.0 g of benzyl deoxycholate and 1.0 g of pyridine were dissolved in 25 ml of dichloromethane, and the solution was ice-cooled. To this solution 2.0 g of bromoacetyl bromide was added dropwise with stirring. The solution was then brought back to room temperature and stirred for 1 hour. To the resultant solution was added 50 ml of chloroform, and the mixture was washed successively with water, 0.5N hydrochloric acid and water. The mixture thus washed was dried over anhydrous magnesium sulfate, and thereafter the solvent was distilled off. The residue was purified by silica gel column chromatography to obtain 2.6 g of benzyl 3-O-bromoacetyl-deoxycholate which was found, when recrystallized from acetonitrile, to have a melting point of 124° to 125° C.

2.0 g of this compound was added to 6 ml of acetone, and 2.8 g of N,N-bis(2-chloroethyl)amine was further added thereto. The solution was stirred for 16 hours at room temperature, and 25 ml of ethyl acetate was added thereto. The resulting solution was washed successively with water, 0.2N hydrochloric acid and water, and then was dried over anhydrous magnesium sulfate, and thereafter the solvent was distilled off. The residue was purified by silica gel column chromatography to obtain 1.8 g of the title compound (yield 42%).

EXAMPLE 37

3-O-[N,N-bis(2-chloroethyl)mminoacetyl] deoxychloic acid 1.0 g of the compound obtained in Example 36 was hydrogenated in 10 ml of tetrahydrofuran in the presence of 400 mg of 5% palladium carbon. The catalyst was then filtered off, and the filtrate was subjected to distillation. The residue was purified by silica gel column chromatography to obtain 520 mg of the title compound (yield 60%).

EXAMPLE 38

3-O-[N,N-bis(2-chloroethyl)aminoacetyl] cholic acid 4.1 g of cholic acid and 0.8 g of pyridine were dissolved in 30 ml of DMF, and the solution was ice-cooled. To this cooled solution 2.2 g of bromoacetyl bromide was added dropwise with stirring. After an hour of stirring at 50° C, the reaction solution was added to 200 ml of water, and a precipitate which was thus formed was taken out by filtration. This precipitate was dissolved in 60 ml of ethyl acetate, and the solution was washed with water. Subsequently, the solution was dried over anhydrous magnesium sulfate, and the solvent was distilled off. The residue was purified by silica gel chromatography to obtain 3.2 g of 3-O-bromoacetyl cholic acid.

3.0 g of this compound was dissolved in acetone, and to the solution was added 1.7 g of N,N-bis(2-chloroethyl)amine. The resulting solution was stirred for 48 hours at room temperature, and the solvent was thereafter distilled off. The residue was purified by silica gel column chromatography to obtain 2.2 g of the title compound (yield 39%) which was found, when recrystallized from chloroform-diisopropyl ether, to have a melting point of 103° to 105° C.

EXAMPLE 39

Benzyl 3-O-[N,N-bis(2-chloroethyl)aminoacetyl]glycocholate 1.2 g of the compound obtained in Example 38, 0.9 g of glycinebenzyl p-triene sulfonate, 0.3 g of triethylamine and 0.44 g of dicyclohexylcarbodiimide were added to 10 ml of ethyl acetate, and the mixture was stirred for 16 hours at room temperature. A precipitate thus formed was filtered off, and to the filtrate was added 40 ml of ethyl acetate. The mixture was washed successively with 0.5N hydrochloric acid and 2% aqueous sodium hydrogencarbonate solution, and then dried over anhydrous magnesium sulfate, and thereafter the solvent was distilled off. The residue was purified by silica gel column chromatography to obtain 850 mg of the title compound (yield 55%).

EXAMPLE 40

3-O-[N,N-bis(2-chloroethyl)aminoacetyl] glycocholic acid 800 mg of the compound obtained in Example 39 was hydrogenated in 20 ml of ethanol in the presence of 300 mg of 5% palladium carbon. The catalyst was then filtered off, and the filtrate was subjected to distillation to remove the solvent and evaporated to dryness under reduced pressure to obtain 650 mg of the title compound (yield 93%).

EXAMPLE 41

3-O-[N,N-bis(2-chloroethyl)aminoacetyl] ursodeoxycholic acid 4.0 g of ursodeoxycholic acid was reacted similarly as in Example 38 to obtain 2.1 g of 3-O-bromoacetyl ursodeoxycholic acid.

1.0 g of this compound was reacted by the procedure of Example 38 on a scale of ⅓ to obtain 800 mg of the title compound (yield 29%) which was found, when recrystallized from ethyl acetate-n-hexane, to have a melting point of 135.5° to 137° C.

EXAMPLE 42

3-O-[N,N-bis(2-chloro-n-propyl)aminoacetyl]ursodeoxycholic acid 1.0 g of the 3-O-bromoacetyl ursodeoxycholic acid obtained in Example 41 was dissolved in 5 ml of acetone, and to the resulting solution was added 2.0 g of N,N-bis(2-chloro-n-propyl)amine (an equivalent mixture of a racemic modification and a meso modification). The resulting solution was stirred for 16 hours at room temperature, and 50 ml of chloroform was then added. The mixture was washed with water, 0.2N hydrochloric acid and water in the order stated, and subsequently dried over anhydrous magnesium sulfate, and thereafter the solvent was distilled off. The residue was purified by silica gel column chromatography to obtain 775 mg of the title compound (yield 26%).

EXAMPLE 43 p-Methoxybenzyl 3-O-[4-(N,N-bis-(2-chloroethyl)amino)-butyryl] deoxycholate 500 mg of 4-[N,N-bis(2-chloroethyl)amino] butyric acid was added to 1 ml of oxalyl chloride. The mixture was stirred for 1 hours at 40° C., distilled under reduced pressure to remove an excess of oxalyl chloride, and evaporated to dryness. The residue was dissolved in 4 ml of dichloromethane, and the solution was added with stirring to 4 ml of a dichloromethane solution containing 1.0 g of p-methoxybenzyl deoxycholate and 0.2 g of pyridine dissolved therein. Fifteen minutes thereafter, 50 ml of chloroform was added to the mixture which was then washed with water and 2% aqueous sodium hydrogencarbonate solution. The mixture thus washed was then dried over anhydrous magnesium sulfate, and the solvent was distilled off. The residue was purified by silica gel column chromatography to obtain 410 mg of the title compound (yield 29%).

EXAMPLE 44

3-O-[4-(N,N-bis(2-chloroethyl)amino)butyryl] deoxycholic acid 250 mg of the compound obtained in Example 43 was reacted similarly as in Example 8 to obtain 150 mg of the title compound (yield 72%).

EXAMPLE 45 p-Methoxybenzyl 3-O-[4-(N,N-bis(2-chloroethyl)amino)-butyryl] chenodeoxycholate 1.0 g of p-methoxybenzyl chenodeoxycholate was reacted similarly as in Example 43 to obtain 300 mg of the title compound (yield 21%).

EXAMPLE 46

3-O-[4-(N,N-bis(2-chloroethyl)amino)butyryl]chenodeoxycholic acid 150 mg of the compound obtained in Example 45 was reacted similarly as in Example 8 to obtain 90 mg of the title compound (yield 72%).

EXAMPLE 47 p-Methoxybenzyl 3-O-[6-(N,N-bis(2-chloroethyl)amino)caproyl] cholate 500 mg of 6-[N,N-bis(2-chloroethyl)amino] caproic acid was added to 1 ml of thionyl chloride, and the mixture was heated under reflux for 1 hour. An excess of thionyl chloride was then distilled off under reduced pressure, and the residue was suspended in 4 ml of dichloromethane. The suspension was added to 5 ml of a dichloromethane solution containing 1.0 g of p-methoxybenzyl cholate and 0.4 g of pyridine dissolved therein. Fifteen minutes thereafter, the mixture was treated similarly as in Example 43 to obtain 350 mg of the title compound (yield 24%).

EXAMPLE 48

3-O-[6-(N,N-bis(2-chloroethyl)amino)caproyl] cholic acid 250 mg of the compound obtained in Example 47 was reacted similarly as in Example 8 to obtain 180 mg of the title compound (yield 85%).

EXAMPLE 49 p-Methoxybenzyl 3-O-[6-(N,N-bis(2-chloroethyl)amino)caproyl] ursodeoxycholate 1.0 g of p-methoxybenzyl ursodeoxycholate was reacted similarly as in Example 47 to obtain 300 mg of the title compound (yield 20%).

EXAMPLE 50

3-O-[6-N,N-bis(2-chloroethyl)amino)caproyl]ursodeoxycholic acid 250 mg of the compound obtained in Example 49 was reacted similarly as in Example 8 to obtain 155 mg of the title compound (yield 52%).

EXAMPLE 51

3-O-[p-(N,N-bis(2-chloroethyl)amino)phenylacetyl]-tauroursodeoxycholic acid 500 mg of 3-O-[p-(N,N-bis(2-chloroethyl)amino)-phenylacetyl] ursodeoxycholic acid, 280 mg of taurine, 300 mg of triethylamine, and 700 mg of 1-ethoxycarbonyl-2-ethoxy-1,2-dihydroquinoline were added to 4 ml of DMF, and the mixture was stirred for 2 hours at 80° C. The reaction solution was added to 150 ml of diisopropyl ether. A precipitate thus formed was washed with 0.2N hydrochloric acid, dried, and purified by silica gel column chromatography to obtain 155 mg of the title compound (yield 27%).

EXAMPLE 52 p-Methoxybenzyl 3-O-[p-(N,N-bis(2-chloroethyl)aminocarbonyloxy)-benzoyl] cholate 530 mg of p-methoxybenzyl cholate and 310 mg of p-N,N-bis(2-chloroethyl)aminocarbonyloxy benzoic acid were reacted similarly as in Example 7 to obtain 235 mg of the title compound (yield 29%).

EXAMPLE 53

3-O-[p-(N,N-bis(2-chloroethyl)aminocarbonyloxy)benzoyl]cholic acid 150 mg of the compound obtained in Example 52 was reacted similarly as in Example 8 to obtain 105 mg of the title compound (yield 82%).

EXAMPLE 54

Benzyl 3-O-[p-(N,N-bis(2-chloroethyl)aminocarbonyloxy)-phenylacetyl] cholate 500 mg of benzyl cholate and 330 mg of p-[N,N-bis(2-chloroethyl)aminocarbonyloxy] phenylacetic acid were reacted similarly as in Example 7 to obtain 305 mg of the title compound (yield 37%).

EXAMPLE 55

3-O-[p-(N,N-bis(2-chloroethyl)aminocarbonyloxy) phenylacetyl] cholic acid 200 mg of the compound obtained in Example 54 was reacted similarly as in Example 18 to obtain 175 mg of the title compound (yield 98%) which was found, when recrystallized from chloroform, to have a melting point of 140° to 143° C.

EXAMPLE 56

3-O-[N,N-bis(2-chloroethyl)aminoacetyl]taurocholic acid 500 mg of 3-O-[N,N-bis(2-chloroethyl)aminoacetyl]-cholic acid was reacted similarly as in Example 51 to obtain 370 mg of the title compound (yield 62%).

PHySIOLOGICAL ACTIyITy

Experimental Example (1) Carcinolytic effect of bile acid derivatives

P388 Mouse leukemia cells which were subjected to passage transplantation in $CDF_1$ mice were suspended in RPMI1640 culture fluid containing 20 mM HEPES to a cell density of $5 \times 10^5$ cells/ml, and 1 ml each of aliquots were apportioned into test tubes. Each of the test samples was added to the suspension to a final concentration of 50 μM, and each preparation was incubated at 37° C with shaking (100 shuttles/min.). Two hours thereafter, $^3H$-thymidine was added to a final concentration of 0.25 μCi/ml, and the incubation was further carried out for 1 hour. Then the radioactivity taken in the cells was measured by a conventional method. The percent inhibition against $^3H$-thymidine intake of the test sample solutions vs. a solvent control is shown in TABLE 2.

TABLE 2

| Test sample | Percent inhibition against $^3H$—thymidine intake (%) |
|---|---|
| Solvent control | 0 |
| Cholic acid | 2 |
| NITROMIN ®* | 52 |
| Compound No. 38 | 83 |
| Compound No. 2 | 90 |
| Compound No. 31 | 94 |
| Compound No. 52 | 88 |

*Nitrogen mustard-N—oxide hydrochloride supplied by Yoshitomi Seiyaku K. K., Tokyo, Japan.

As is apparent from the above TABLE, the bile acid derivatives of the present invention were found to have far higher inhibitory activity against $^3H$-thymidine intake of the P388 leukemia cells as compared with a negative control cholic acid.

Microscopic observation further revealed that the extents of degeneration and necrosis of the cells were closely correlated with the percent inhibition against $^3H$-thymidine intake.

(2) Toxicity 2,000 mg/kg of the bile acid derivative of the present invention (Compound No. 38) (prepared with a 0.5% CMC solution) was administered orally once to a group of four male ICR mice, and their life spans were observed for 3 weeks.

Separately, 500 mg/kg of the above test compound was administered intraperitoneally to a group of eight male ICR mice, and their life spans were similarly observed for 3 weeks.

No mortality case was observed in either group of mice, and therefore the bile acid derivative of the present invention can be said to be generally of low toxicity.

We claim:

1. A bile derivative of the following formula (I):

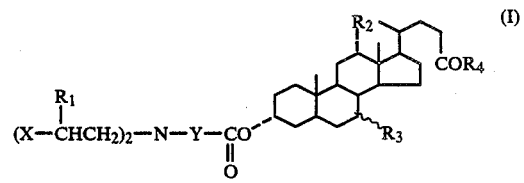

wherein: X is a halogen atom; $R_1$ is a hydrogen atom or a lower alkyl group; y is

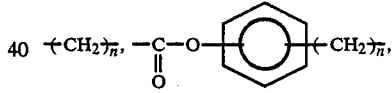

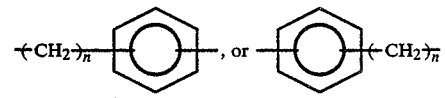

wherein n is an integer of from 1 to 5; each of $R_2$ and $R_3$ is a hydrogen atom or a hydroxyl group; $R_4$ is a hydroxyl group, lower alkoxyl group,

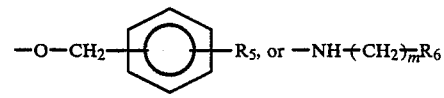

wherein $R_5$ is a hydrogen atom or a lower alkoxyl group, $R_6$ is a carboxyl group, benzyloxycarbonyl group or sulfonyl group, or a salt thereof, and m is an integer of from 1 to 4; the intermittent line, . . . , is an α-bond; or the wavy line, ∿∿∿, is an α- or β-bond, and a salt thereof.

2. A bile acid derivative according to claim 1 wherein the lower alkoxyl group of $R_4$ has 1 to 4 carbon atoms.

3. A process for producing a bile acid derivative of the following formula (I):

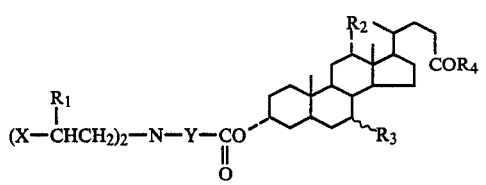 (I)

wherein: X is a halogen atom; $R_1$ is a hydrogen atom or a lower alkyl group; y is

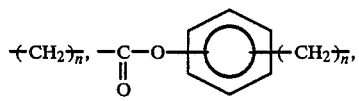

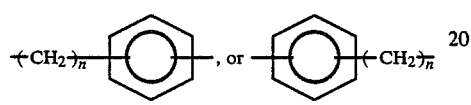

wherein n is an integer of from 1 to 5; each of $R_2$ and $R_3$ is a hydrogen atom or a hydroxyl group; $R_4$ is a hydroxyl group, lower alkoxyl group,

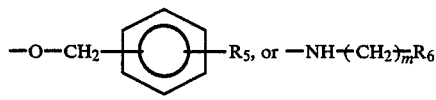

wherein $R_5$ is a hdyrogen atom or a lower alkoxyl group, $R_6$ is a carboxyl group, benzyloxycarbonyl group of sulfonyl group, or a salt thereof, and m is an integer of from 1 to 4; the intermittent line, . . . , is an α-bond; and the wavy line,⁓, is an α- or β-bond; or a salt thereof, which comprises the step (a), the steps (a) and (b), or the steps (a), (b) and (c) set forth below:
(a) causing a bile acid derivative of the following formula (II):

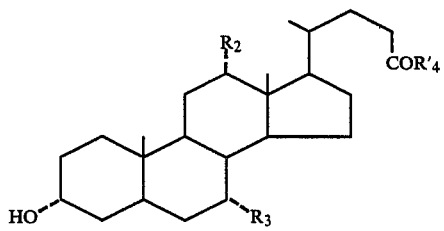 (II)

wherein: each of $R_2$ and $R_3$ is a hydrogen atom or a hydrogen group; $R'_4$ is a lower alkoxyl group or

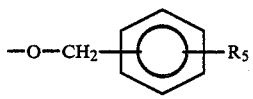

wherein $R_5$ is a hydrogen atom or a lower alkoxyl group; the intermittent line, . . . , is an α-bond; and the wavy line,⁓, is an α- or β-bond, to react with a compound of the following formula (III):

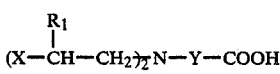 (III)

wherein: X is a halogen atom; $R_1$ is a hydrogen atom or lower alkyl group; and y is

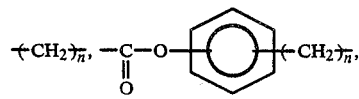

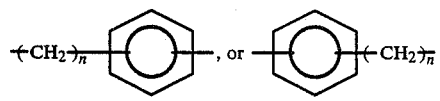

wherein n is an integer of 1 to 5, thereby to obtain the bile acid derivative of the above formula (I) wherein $R_4$ is the same as $R'_4$;
(b) subjecting the bile acid derivative obtained in the above step (a) wherein $R_4$ is

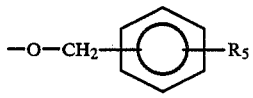

to acid treatment or to catalytic reduction to obtain the bile acid derivative of the above formula (I) wherein $R_4$ is a hydroxyl group; and
(c) causing the bile acid derivative obtained in the preceding step (b) to react with a compound of the formula (Iy);

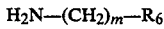  (Iy)

wherein $R_6$ is a carboxyl group, benzyloxycarbonyl group or sulfonyl group which may be in salt form, and m is an integer of 1 to 4, to obtain the bile acid derivative of the above formula (I) wherein $R_4$ is $-NH-(CH_2)_m-R_6$.

4. A process according to claim 3, wherein the lower alkoxyl group of $R_4$ has 1 to 4 carbon atoms.

* * * * *